United States Patent [19]

Gesswein et al.

[11] Patent Number: 5,390,678
[45] Date of Patent: Feb. 21, 1995

[54] METHOD AND DEVICE FOR MEASURING ULTRANSONIC ACTIVITY IN AN ULTRASOUND DELIVERY SYSTEM

[75] Inventors: Douglas H. Gesswein, Mission Viejo; Timothy C. Mills, Newport Beach; Pete B. Klumb, Corona Del Mar, all of Calif.

[73] Assignee: Baxter International Inc., Deerfield, Ill.

[21] Appl. No.: 134,559

[22] Filed: Oct. 12, 1993

[51] Int. Cl.⁶ .............................................. A61B 8/12
[52] U.S. Cl. ................................. 128/662.06; 604/22; 128/660.03
[58] Field of Search ...................... 128/660.07, 661.01, 128/660.04, 662.03, 662.06, 660.03; 73/625; 601/2; 604/22; 606/2.5

[56] References Cited

U.S. PATENT DOCUMENTS

| | | |
|---|---|---|
| 3,352,303 | 11/1967 | Delaney . |
| 3,433,226 | 3/1969 | Boyd . |
| 3,526,219 | 9/1970 | Balamuth . |
| 3,565,062 | 3/1971 | Kuris . |
| 3,589,363 | 6/1971 | Banko . |
| 3,618,594 | 11/1970 | Banko . |
| 3,809,093 | 5/1974 | Abraham . |
| 3,823,717 | 7/1974 | Pohlman . |
| 3,861,391 | 1/1975 | Antonevich et al. . |
| 3,896,811 | 7/1975 | Storz . |
| 4,188,952 | 2/1980 | Loschivlov et al. . |
| 4,214,586 | 7/1980 | Mericle . |
| 4,223,676 | 9/1980 | Wuchinich et al. . |

(List continued on next page.)

FOREIGN PATENT DOCUMENTS

| | | |
|---|---|---|
| 0424231 | 4/1984 | European Pat. Off. . |
| 189329 | 7/1986 | European Pat. Off. . |
| 293472 | 11/1986 | European Pat. Off. . |
| 316796 | 11/1986 | European Pat. Off. . |
| 208175 | 1/1987 | European Pat. Off. . |
| 0209468 | 1/1987 | European Pat. Off. . |
| 234951 | 2/1987 | European Pat. Off. . |
| 347098 | 6/1989 | European Pat. Off. . |
| 315290 | 10/1989 | European Pat. Off. . |
| 443256 | 12/1990 | European Pat. Off. . |
| 472368 | 2/1992 | European Pat. Off. . |
| 2424733 | 11/1980 | France . |
| 2641693 | 7/1990 | France . |
| 2643272 | 8/1990 | France . |
| 2349120 | 4/1975 | Germany . |
| 2438648 | 2/1976 | Germany . |
| 2453126 | 5/1976 | Germany . |

(List continued on next page.)

OTHER PUBLICATIONS

Circulation, vol. 81, No. 2, Feb. 1990, "Application of a New Phased-Array Ultrasound Imaging Catheter in the Assessment of Vascular Dimensions," pp. 660–666.
"Ultrasonic Energy Causes Doe-Dependent, Endothelium-Independent Arterial Relaxation"–T. Fischell, et al. Abstracts of the 63rd Scientific Sessions, pp. 111–219.

*Primary Examiner*—George Manuel
*Attorney, Agent, or Firm*—Stetina & Brunda

[57] ABSTRACT

A device for measuring ultrasonic activity in an ultrasound delivery system has a sensor for providing an output representative of a sensed ultrasound vibration level, an indicator for receiving the output of the sensor and providing an indication of the vibration level sensed thereby, and a rigid body to which the sensor is attached. The rigid body comprises a sensor attaching portion and a catheter abutting portion configured to abut the distal end of an ultrasound delivery system catheter. Ultrasonic activity of the ultrasound delivery system is measured by abutting the distal end of the catheter to the catheter abutting portion of the rigid body and noting the indication provided by the indicator. Use of a disposable sterile catheter abutting portion removeably attachable to the sensor attaching portion facilitates isolation of the sensor attaching portion within a bag along with an ultrasound transducer.

23 Claims, 4 Drawing Sheets

U.S. PATENT DOCUMENTS

| | | | |
|---|---|---|---|
| 4,366,819 | 1/1983 | Kaster. | |
| 4,413,630 | 11/1983 | Anderson et al. | 128/660.04 |
| 4,431,006 | 2/1984 | Trimmer et al.. | |
| 4,474,180 | 10/1984 | Angulo. | |
| 4,587,958 | 5/1986 | Noguchi et al.. | |
| 4,587,972 | 5/1986 | Morantte. | |
| 4,589,419 | 5/1986 | Laughlin et al.. | |
| 4,593,699 | 6/1986 | Poncy et al. | 128/662.03 |
| 4,633,882 | 1/1987 | Matsuo et al. | 128/662.06 |
| 4,665,906 | 5/1987 | Jervis. | |
| 4,692,139 | 9/1987 | Stiles. | |
| 4,750,902 | 6/1988 | Wuchinich et al.. | |
| 4,794,931 | 1/1989 | Yock. | |
| 4,799,496 | 1/1989 | Hargraves. | |
| 4,800,876 | 1/1989 | Fox et al.. | |
| 4,808,153 | 2/1989 | Parisi. | |
| 4,821,731 | 4/1989 | Martnelli. | |
| 4,841,977 | 6/1989 | Griffith. | |
| 4,844,092 | 7/1989 | Rydell. | |
| 4,852,577 | 8/1989 | Smith et al. | 128/660.07 |
| 4,870,953 | 10/1989 | DonMichael. | |
| 4,898,575 | 2/1990 | Fischell et al.. | |
| 4,917,097 | 4/1990 | Proudian et al.. | |
| 4,919,133 | 4/1990 | Chiang. | |
| 4,920,954 | 5/1990 | Alliger et al.. | |
| 4,923,441 | 5/1990 | Shuler. | |
| 4,924,863 | 5/1990 | Sterzer. | |
| 4,936,281 | 6/1990 | Stasz. | |
| 4,957,111 | 9/1990 | Millar. | |
| 4,960,411 | 10/1990 | Buchbinder. | |
| 4,966,583 | 10/1990 | Debbas. | |
| 4,967,653 | 11/1990 | Hinz. | |
| 4,967,753 | 11/1990 | Haase et al.. | |
| 4,979,939 | 12/1990 | Shiber. | |
| 4,988,356 | 1/1991 | Crittenden. | |
| 4,998,527 | 3/1991 | Meyer. | |
| 5,022,399 | 6/1991 | Biegeleisen. | |
| 5,029,588 | 7/1991 | Yock et al.. | |
| 5,058,570 | 10/1991 | Idemoto et al.. | |
| 5,061,238 | 10/1991 | Shuler. | |
| 5,069,664 | 12/1991 | Guess et al.. | |
| 5,076,276 | 12/1991 | Sakurai et al.. | |
| 5,100,423 | 3/1992 | Fearnot. | |

FOREIGN PATENT DOCUMENTS

| | | |
|---|---|---|
| 2541919 | 3/1977 | Germany. |
| 2703486 | 12/1977 | Germany. |
| 8119209 | 10/1981 | Germany. |
| 3726210 | 8/1987 | Germany. |
| 3707567 | 9/1987 | Germany. |
| 3707921 | 9/1987 | Germany. |
| 3826414 | 2/1989 | Germany. |
| 3812836 | 4/1990 | Germany. |
| 4114826 | 5/1991 | Germany. |
| 1520448 | 7/1975 | United Kingdom. |
| 2208138A | 3/1989 | United Kingdom. |
| 2212267 | 7/1989 | United Kingdom. |
| WO87/01276 | 3/1987 | WIPO. |
| WO87/05793 | 10/1987 | WIPO. |
| WO89/05123 | 6/1989 | WIPO. |
| WO89/06515 | 7/1989 | WIPO. |
| WO89/07419 | 8/1989 | WIPO. |
| WO90/01300 | 2/1990 | WIPO. |
| WO90/07303 | 7/1990 | WIPO. |
| WO91/02489 | 3/1991 | WIPO. |
| WO91/14401 | 10/1991 | WIPO. |
| WO92/10140 | 6/1992 | WIPO. |
| WO92/11815 | 7/1992 | WIPO. |

METHOD AND DEVICE FOR MEASURING ULTRANSONIC ACTIVITY IN AN ULTRASOUND DELIVERY SYSTEM

FIELD OF THE INVENTION

The present invention relates generally to medical devices and more particularly to a method and device for measuring ultrasonic activity in an ultrasound delivery system so as to assure proper operation of the ultrasound delivery system during therapeutic procedures.

BACKGROUND OF THE INVENTION

A number of ultrasonic devices have heretofore been proposed for use in ablating or removing obstructive material from anatomical structures, such as blood vessels. Examples of devices which purportedly utilize ultrasonic energy, alone or in conjunction with other treatment modalities, to remove obstructions from anatomical structures include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Alliger, et al.), and 5,100,423 (Fearnot) as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2,438,648 (Pohlman).

Ultrasound transmitting catheters have been utilized to successfully ablate various types of obstructions from blood vessels of humans and animals. Particular success has been achieved in ablation of obstructions located in peripheral blood vessels such as the femoral arteries. Successful application of ultrasonic energy to smaller blood vessels, such as the coronary arteries, has also been achieved. Such applications necessitate the use of ultrasound transmitting catheters which are sufficiently small and flexible to undergo transluminal advancement through the tortuous vasculature of the aortic arch and coronary tree.

Additionally, ultrasound transmitting catheters may be utilized to deliver ultrasonic energy to blood vessel walls for the purpose of preventing or reversing vasospasm as described in copending U.S. patent application Ser. No. 07/911,651, entitled ANGIOPLASTY AND ABLATIVE DEVICES HAVING ONBOARD ULTRASOUND COMPONENTS AND DEVICES AND METHODS FOR UTILIZING ULTRASOUND TO TREAT OR PREVENT VASOSPASM.

Thus, it is apparent that the use of ultrasound therapeutic procedures provides substantial benefits. However, a problem commonly associated with the performance of such procedures is the inability to readily determine proper functioning of the ultrasound delivery system. As those skilled in the art will appreciate, the presence of the desired level of ultrasound energy at the distal end of the ultrasound catheter cannot be determined by visual inspection or feel. Thus, the operator cannot easily ascertain whether or not the ultrasound delivery system is providing the desired level of ultrasound energy at the distal end of the ultrasound catheter.

It is necessary that the ultrasound delivery system be functioning properly in order to provide the desired therapeutic effect. It is common for ultrasound delivery systems to function suboptimally or not at all due to loose mechanical connection of the ultrasound transmission member, breakage of the ultrasound transmission member, failure of the ultrasound transducer, and failure of the ultrasound generator and control electronics, as well as for various other reasons.

Various things can happen to the different components of the ultrasound delivery system during shipping, handling, and use thereof so as to cause the ultrasound delivery system to function suboptimally. For example, rough handling of the piezoelectric crystal of the ultrasound transducer can result in damage thereto which causes the system to function at less than the desired level and which is not readily apparent to the user. The piezoelectric crystal itself may become cracked or broken, or the electrical leads thereto may fail so as to provide inadequate electrical conduction. Indeed, a wide variety of different types of malfunctions and component failures may occur so as to render operation of the ultrasound delivery system suboptimal.

It is also possible for the operator to improperly set up or operate the ultrasound delivery system so as to inadvertently cause the system to operate suboptimally. For example, an inappropriate level of ultrasound vibration may inadvertently be selected by the operator, thus potentially rendering the therapeutic procedure ineffective. For example, a level of ultrasound vibration appropriate for coronary procedures may inadvertently be selected when a peripheral procedure is to be performed. The level of ultrasound vibration commonly associated with coronary procedures is substantially lower than that generally desired for use in peripheral procedures. Thus, even though a visual indication, e.g., status light or digital readout, of the selected procedure may be provided at the signal generator, it is possible for the operator to overlook such visual indication and to perform the procedure at an ultrasound energy level other than that desired.

Thus, it is possible to perform an entire therapeutic procedure with an ultrasound delivery system providing suboptimal or zero output and without the operator being aware of such problem. Contemporary methodology provides no means for assuring proper operation of the ultrasound delivery system during therapeutic procedures.

The performance of such therapeutic procedures with an ultrasound delivery system providing suboptimal or no ultrasound energy has potentially serious consequences for the patient. For example, rather than ablating the material comprising a stenosis, the distal end of the catheter may undesirably dislodge portions thereof or may compact the stenotic material against the vessel walls. Such breaking away of stenotic material or compaction thereof may go unnoticed until a serious problem caused thereby arises. Stenotic debris may potentially form an embolism, thus impeding the flow of blood to a vital organ, e.g., the brain. Compaction of stenotic material may provide a base upon which further stenotic material may subsequently accumulate.

As such, it would be beneficial to verify proper operation of the ultrasound delivery system prior to commencing the therapeutic procedure for which the ultrasound delivery system is to be utilized.

SUMMARY OF THE INVENTION

The present invention specifically addresses and alleviates the above mentioned deficiencies associated with the prior art. More particularly, the present invention comprises a method and device for measuring ultrasonic activity in an ultrasound delivery system so as to assure proper operation of the ultrasound delivery system during therapeutic procedures. Thus, the undesirable consequences of equipment malfunction and operator error are mitigated. The device for measuring ultrasonic activity in an ultrasound delivery system comprises a sensor for providing an output representative of a sensed ultrasound vibration level, an indicator for receiving the output of the sensor and providing an indication of the vibration level sensed thereby, and a rigid body to which the sensor is attached. The rigid body comprises a sensor attaching portion configured to receive a sensor and a catheter abutting portion configured to abut the distal end of an ultrasound delivery system catheter. The catheter abutting portion, the sensor attaching portion, and the sensor, taken together, define a sensing head. Ultrasonic activity of the ultrasound delivery system is measured by abutting the distal end of the catheter to the catheter abutting portion of the rigid body and then noting the indication provided by the indicator.

The sensor preferably comprises an accelerometer apparatus and the indicator preferably comprises a meter apparatus. Those skilled in the art will recognize that various other types of sensors are likewise suitable. For example, a displacement sensor or a velocity sensor may alternatively be utilized and the output thereof optionally converted to acceleration so as to facilitate use thereof in combination with a meter apparatus configured to receive an acceleration signal. Alternatively, the meter apparatus may directly use the output of such a displacement sensor or velocity sensor.

The meter apparatus preferably comprises a voltmeter apparatus configured to provide an indication of the ultrasound vibration level. Those skilled in the art will recognize various types of meter apparatus and indications are likewise suitable. For example, a digital readout of the acceleration, velocity, and/or displacement of the distal end of the ultrasound catheter may be provided.

The sensor attaching portion preferably comprises a female threaded coupling and the sensor, e.g., accelerometer apparatus, preferably comprises a male threaded coupling engaging the female threaded coupling so as to provide rigid attachment of the accelerometer to the rigid body. The catheter abutting portion preferably comprises a recess configured to receive the distal end or end of the ultrasound delivery system catheter.

The recess may optionally be configured to conform to the shape of the distal end of the ultrasound catheter. Alternatively, the recess may merely be a dimple or bore configured so as to receive the distal end of the ultrasound catheter. Those skilled in the art will appreciate that various different configurations of the recess are likewise suitable.

The catheter abutting portion is removeably and rigidly attachable to the sensor attaching portion so as to facilitate placement of the sensor attaching portion upon one side of a sterile barrier and placement of the catheter abutting portion upon the opposite side of the sterile barrier. The sterile barrier is thus captured intermediate the sensor attaching portion and the catheter abutting portion.

The catheter abutting portion is preferably maintained in a sterile condition, e.g., disposed within a sterile enclosure, prior to use thereof. The catheter abutting portion is preferably disposable, such that a new, sterile catheter abutting portion is utilized for each therapeutic procedure. In the preferred embodiment of the present invention each catheter abutting portion is thus maintained in a sterile condition within a sealed plastic package prior to use thereof and is disposed of after each use.

The indicator is preferably configured so as to provide an indication of the condition of ultrasound delivery systems providing various different desired ultrasonic activity levels so as to accommodate various different therapeutic procedures. Thus, for example, the operator may select the particular therapeutic procedure, e.g., coronary or peripheral, which is to be performed so as to utilize the device for measuring ultrasonic activity of the present invention to verify proper operation of the ultrasound delivery system for the particular therapeutic procedure to be performed.

In this regard, the device for measuring ultrasound activity of the present invention preferably comprises a selector for selecting the type of procedure in which the ultrasound delivery system is to be utilized. The indication of the condition of the ultrasound delivery system is responsive to the selector. The selector causes the attenuation or amplification of the sensor signal so as to provide an accurate indication of the acceptability thereof.

A method for performing therapeutic ultrasound procedures according to the present invention generally comprises measuring ultrasound activity in the ultrasound delivery system prior to commencing ultrasound therapy and preferably repeating measurement of the ultrasound activity subsequent to the therapeutic procedure so as to verify continued proper operation of the ultrasound delivery system during the therapeutic procedure.

The method more particularly comprises the steps of activating the ultrasound delivery system, abutting a distal end of an ultrasound catheter of the ultrasound delivery system to a device for measuring ultrasonic activity, and noting the level of ultrasonic activity as indicated by an indicator responsive to the device for measuring ultrasonic activity. The method preferably further comprises the step of selecting the desired procedure to be performed, the indicator being responsive to such selection so as to indicate whether the measured level of ultrasonic activity is sufficient for performance of the particular selected procedure or, alternatively, is insufficient for performance of the particular selected procedure. The level of ultrasonic activity preferably is indicated as a fail/pass indication.

The step of abutting a distal end of an ultrasound catheter to a device for measuring ultrasonic activity preferably comprises abutting the distal end of the catheter to a catheter abutting portion formed upon a rigid body, the rigid body having a sensor attached thereto for providing an output to the indicator representative of the level of ultrasound vibration sensed thereby.

The method preferably further comprises the step of attaching the catheter abutting portion to the sensor attaching portion of the rigid body so as to capture a sterile barrier, e.g., a bag, therebetween. Thus, the sensor attaching portion of the rigid body need not be maintained in a sterile condition. The sensor attaching portion of the rigid body is disposed within a sterile bag so as to isolate it from the sterile environment in which the ultrasound procedure is being performed. The ultrasound transducer is likewise disposed within the sterile bag and attached to the ultrasound catheter which extends therefrom. Only the catheter abutting portion of the rigid body needs to be maintained in a sterile condition, since the catheter abutting portion is disposed outside of the sterile bag during performance of the ultrasound therapeutic procedure. Similarly, the ultrasound catheter is typically maintained in a sterile condition prior to use and is likewise typically disposable.

Thus, according to the methodology of the present invention, an ultrasound transducer is disposed within a sterile bag such that a sterile ultrasound catheter extends from the bag and a rigid body having an ultrasound vibration sensor attached thereto is likewise disposed within the sterile bag. A catheter abutting portion of the rigid body is rigidly attached thereto such that the catheter abutting portion is disposed outside of the bag. The ultrasound delivery system is then activated and the distal end of the ultrasound catheter abutted to the catheter abutment end member of the rigid body so as to transmit ultrasound vibration thereto. The level of the ultrasonic activity as indicated by the indicator is then noted and preferably provides a fail/pass indication.

The particular procedure to be performed is preferably selected at the indicator such that the indication provided by the indicator is specific to the level of ultrasound vibration required for the selected procedure.

Measurement of the ultrasound activity at the distal end of the ultrasound catheter is preferably repeated after performance of the ultrasound therapeutic procedure so as to verify continued proper operation of the ultrasound delivery system throughout the procedure.

These, as well as other advantages of the present invention will be more apparent from the following description and drawings. It is understood that changes in the specific structure or methodology described herein may be made within the scope of the claims without departing from the spirit of the invention.

DETAILED DESCRIPTION OF THE PREFERRED EMBODIMENT

The following detailed description and the accompanying drawings are intended to describe and show presently preferred embodiment(s) of the invention only and are not intended to limit the scope of the invention in any way.

a. A Preferred Vibration Measuring Device

Figure 1:
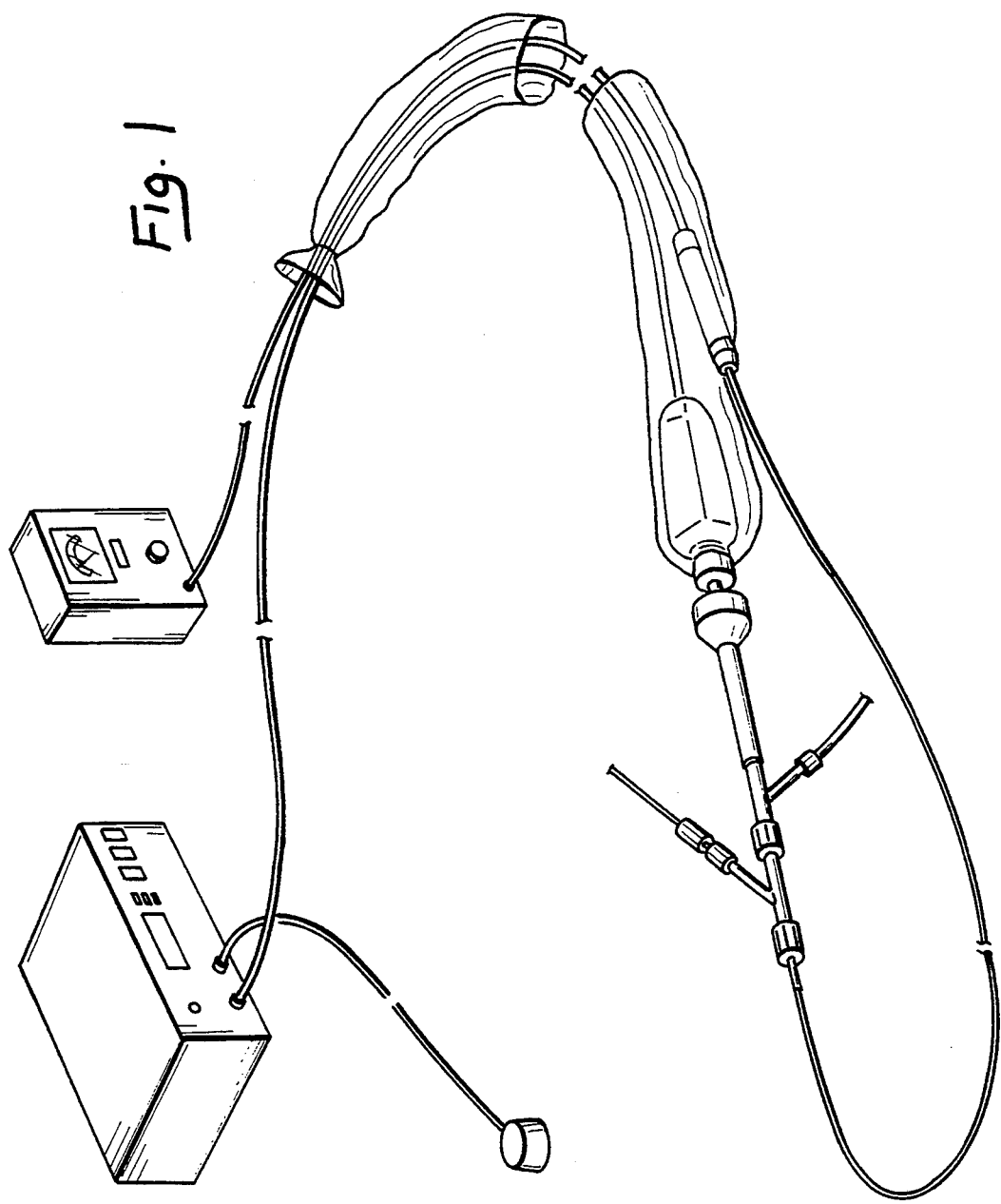
FIG. 1 is a perspective view of the device for measuring ultrasonic activity in an ultrasound delivery system of the present invention being utilized within a contemporary ultrasound delivery system.
Figure 2:
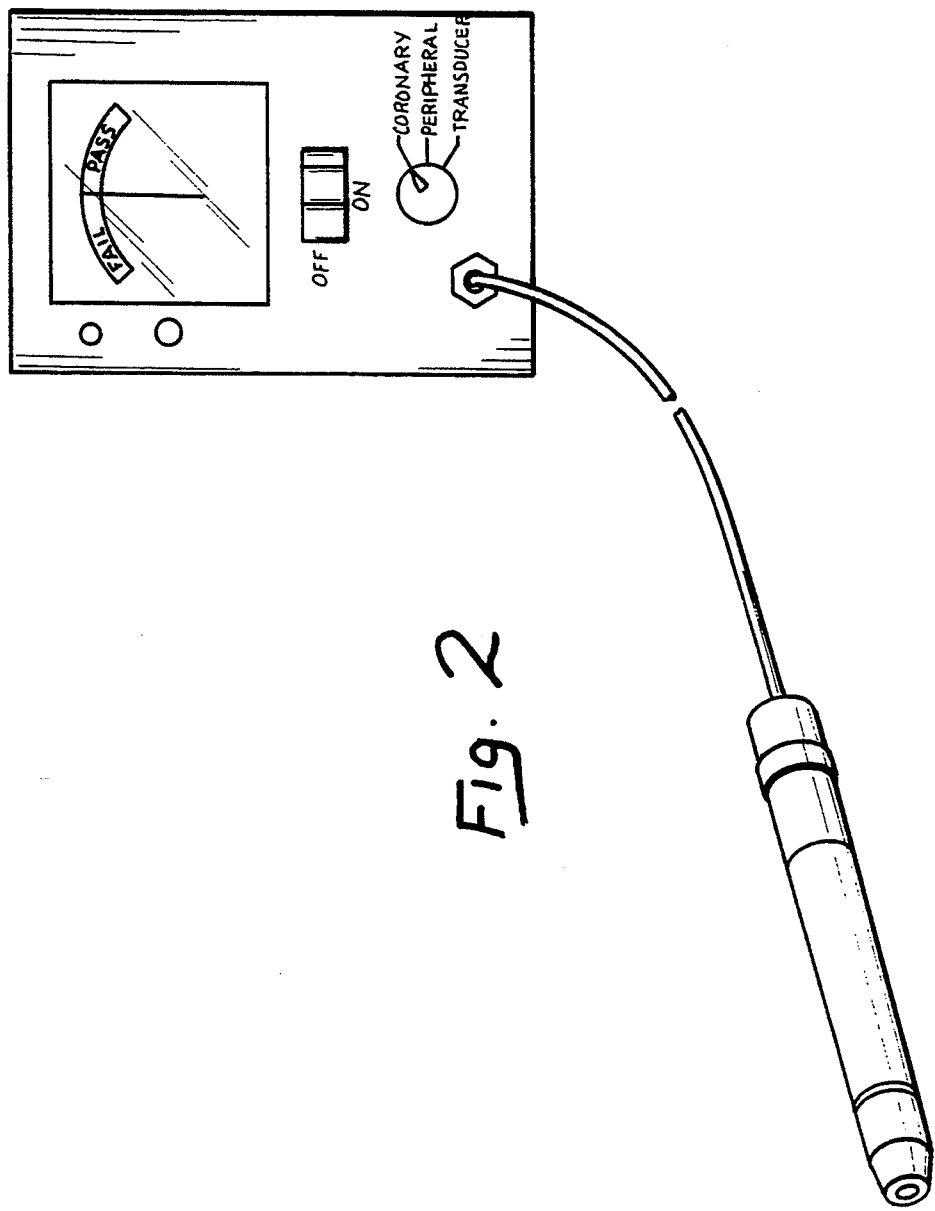
FIG. 2 is an enlarged perspective view of the device for measuring ultrasound activity of FIG. 1.

As shown in FIGS. 1 and 2, the device of the present invention may be utilized to measure the vibrational output of a medical ultrasound catheter prior to insertion of the catheter into a mammalian body.

As shown, the device 10 of the present invention generally comprises a vibration sensing head 12 connected to a meter apparatus 14.

Figure 3:
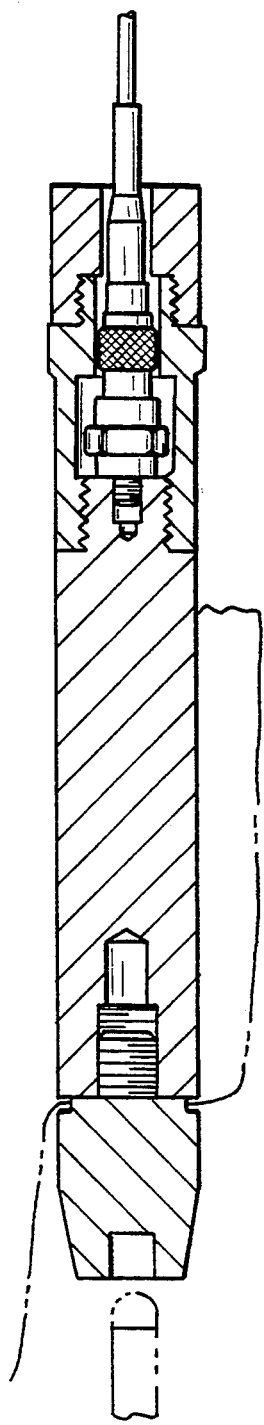
FIG. 3 is a cross-sectional side view of the sensing head of FIG. 2, shown in cross-section.
Figure 4:
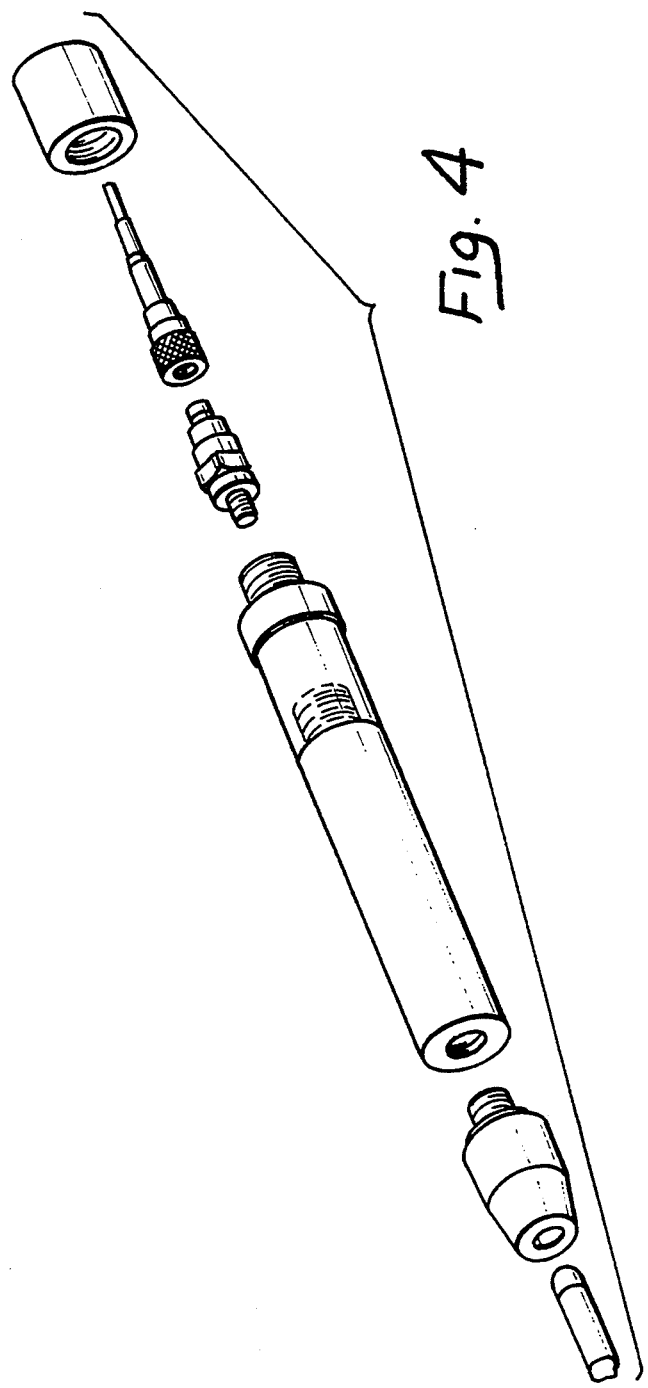
FIG. 4 is an exploded perspective view of the sensing head of FIG. 3.

The vibration sensing head 12, described in more detail herebelow and shown in FIGS. 3-4, generally consists of an elongate rigid housing 16 connectable to a disposable abutment end member 18.

The rigid housing 16, as well as the abutment end member 18 and the sleeve 56, are preferably comprised of a polymer, preferably acetal resin (e.g., Delrin TM manufactured by Du Pont De Nemours, E. I., and Co., Inc.). The rigid body member 52 is preferably approximately 3.150 inches long from the deepest portion of the recess 42 to the accelerometer 50 (dimension A of FIG. 3). The diameter of the rigid body member 52 is preferably approximately 0.600 inch (Dimension B of FIG. 3). Those skilled in the art will recognize that various other substantially rigid materials and various other dimensions and configurations of the rigid body member 52 are likewise suitable.

The meter apparatus 14 of the device 10 preferably comprises a voltmeter apparatus having a readout or display 72 which is calibrated or delineated to indicate either acceptable (i.e., "pass") or non-acceptable (i.e., "fail") levels of vibrational energy sensed by the device 10.

As shown in FIG. 1, the device 10 of the present invention may be utilized in conjunction with a medical ultrasound catheter system. The typical medical ultrasound catheter system comprises an elongate catheter 20 having a proximal end and a distal end. A proximal end connector assembly 22 is positioned on the proximal end of the catheter 20 and is coupleable to an ultrasound transducer 24. The ultrasound transducer 24 is connected by way of cable 26 to signal generator 28. Signal generator 28 is provided with an on/off foot pedal 30. Depression of on/off foot pedal 30 causes signal generator 28 to emit an electrical signal through cable 26 to ultrasound transducer 24. Ultrasound transducer 24 converts the electrical signal received thereby to ultrasonic vibration. An ultrasound transmission member or wire (not shown) extends longitudinally through the length of the catheter 20 so as to transmit the ultrasonic vibration from transducer 24 to the distal end DE of the catheter 20.

Various untoward circumstances may result in disruption or mutation of the ultrasonic vibration transmitted to the distal end DE of the catheter 20. For example, if the ultrasound transmission member or wire (not shown) should become fractured or broken, such may significantly diminish the quantum of ultrasonic vibration transmitted to the distal end DE of the catheter 20. Similarly, if the connection between the proximal connector assembly 22 and the ultrasound transducer 24 has been disrupted, there will be a resultant diminution or interruption of the ultrasonic energy transmitted to the distal end DE of the catheter 20. Also, if the signal generator 20 or transducer 24 were to have been improperly set, or malfunctioning, such may also result in an incorrect amount of ultrasound vibration reaching the distal end DE of the catheter 20.

If, in fact, the desired level of vibrational energy is not being transmitted to the distal end DE of the catheter 20, it is desirable to determine such fact before the catheter 20 has been inserted into the patient. Thus, the device 10 of the present invention may be utilized to test the ultrasonic vibration at the distal end DE of the catheter 20 prior to insertion of the catheter so that adjustments or remedial measures may be undertaken before the catheter 20 is inserted into the patient.

As shown in FIG. 1, it is preferable that the catheter 20 be maintained in a sterile condition during the testing procedure. Accordingly, the accelerometer apparatus housing portion 16 of the sensing head 12 is initially inserted into a sterile barrier bag 40 or sheath defining a sterile barrier, along with the non-sterile ultrasound transducer 24. One commercially sterile barrier bag which may be utilized for this purpose is the Baxter TM Arthroscopy Camera Drape (Sterile) available from Baxter Healthcare Corporation, Hospital Supply Division, Deerfield, Ill. 60015. Thereafter, the sterile disposable catheter abutting end member 18 is screwed onto the distal end of the accelerometer apparatus housing portion 16 of the sensing head 12, outside of the sterile barrier bag 40 such that a portion of the material of the sterile barrier bag 40 is trapped or clamped between the non-sterile accelerometer apparatus housing portion 16 and the sterile disposable catheter-abutting end member 18. Similarly, the proximal connector assembly 22 of the catheter 20 is threaded onto and coupled to the ultrasound transducer 24 with the sterile barrier bag 40 being tightly closed therearound so as to maintain the proximal connector assembly 22 of the catheter within the sterile field.

After the catheter 20 has been operatively connected to the ultrasound transducer 24, the distal end DE of the catheter 20 is inserted into the catheter receiving recess or well formed in the distal end of the catheter abutting end member 18. The distal end DE of the catheter 20 is held in firm abutting contact with the floor of the recess 42 and the on/off foot pedal 30 of the signal generator 28 is utilized to activate signal generator 28. Signal generator 28 is typically preset at a desired output level expected to provide the acceptable ultrasonic vibration at the distal end DE of the catheter 20.

As the signal passes from signal generator 28 through cable 26, the ultrasound transducer 24 will convert the signal to ultrasonic vibration. The ultrasonic vibration then will be transmitted through catheter 20 to the distal end DE thereof.

Abutment of the distal end DE of the catheter 20 with the floor of the catheter receiving recess 42 of the probe member 12 causes the vibration of the distal end DE to be sensed by accelerometer apparatus 50 and converted thereby into an electrical signal. The electrical signal is then transmitted through cable 13 to monitor 14 and a corresponding acceptable/unacceptable indication is displayed by monitor 14 as a result of the vibrational energy sensed by the accelerometer apparatus 50 of the sensing head 12.

Depending on the intended therapeutic application of the ultrasound system, the signal generator 28 and monitor 14 may be specifically set to desired ranges or energy levels pre-determined to be suitable for the intended therapeutic application. For example, in clinical settings wherein the catheter 20 is to be inserted into a blood vessel for purposes of ablating or ultrasonically treating vaso-obstructive matter within the blood vessel, the setting of the signal generator 28 may differ depending on whether the obstruction to be treated is within the coronary or peripheral vasculature. Accordingly, the mode setting apparatus 44 of monitor 14 may be appropriately set on "coronary" or "peripheral" settings such that the monitor 14 will be thereby adjusted to seek the appropriate vibrational levels for the intended "coronary" or "peripheral" use.

Additionally, the device 10 of the present invention may be utilized to test the vibrational output of the ultrasound transducer 24 itself, without the attachment of the catheter 20. When utilized for such purpose, the mode setting apparatus 44 of monitor 14 will be switched to its "transducer" setting and the distal end of the transducer horn will be inserted into the recess 42 of the sensing head 12, in firm abutment therewith. As such, the vibrational energy emanating from the horn of the transducer 24 will be sent by the accelerometer apparatus 50 of the probe and, provided that the mode setting apparatus 44 of the monitor 14 is appropriately set on the "transducer" setting, the monitor will display an indication as to whether the vibrational energy sensed by the accelerometer apparatus is within the desirable range defined for the transducer test.

b. Preferred Construction of the Vibration Sensing Head

The vibration sensing head 12 of the device 10 may constructed and configured in various ways. One presently preferred mode of constructing the vibration sensing head 12 as shown in FIGS. 3 and 4.

As shown, the presently preferred sensing head 12 comprises a detachable abutment end member 18, a rigid body 52, an accelerometer apparatus 50, an accelerometer apparatus cable connector 54 and a guide sleeve 56.

A threaded male projection 58 is formed on the proximal side of abutment end member 18. A corresponding threaded female bore is formed in the distal end of rigid body member 52. By such construction, the threaded male projection 58 of the abutment end member 18 may be screwed into the threaded female bore 60 of the rigid body member 52, thereby pinching or trapping the sterile barrier 40 therebetween, as shown in FIG. 3.

A proximal accelerometer apparatus housing member 62 is mounted on the proximal end of rigid body member 52. The proximal accelerometer apparatus housing member 62 has an inner bore 66 which is sized and configured to receive accelerometer apparatus 50 therewithin. A threaded accelerometer apparatus receiving bore 66 is formed in the proximal end of rigid body member 52. A corresponding threaded male projection 64 is formed on the distal face of accelerometer apparatus 50 such that accelerometer apparatus 50, when inserted into the inner bore 66 of accelerometer apparatus housing member 62, may be firmly threaded into bore 66, thereby causing accelerometer apparatus 50 to be firmly and rigidly mounted in abutting contact with the rigid body member 52. As such, vibrational energy received by the distal end member 18 will be transmitted through the rigid body member 52 and will be sensed by accelerometer apparatus 50.

One commercially available accelerometer which may be incorporated into the device of the present invention is the PCB Piezotronics, Inc., model number 353B18 quartz shear mode accelerometer apparatus, such as that available from PCB Electronics, 3425 Walden Avenue, Depew, N.Y. 14043-2495 having a sensitivity of 10 Mv/g and a frequency range of 0.35 to 30,000 Hz ($+/-3$ Db). Those skilled in the art will recognize that various other accelerometer apparatus and/or vibration sensors are likewise suitable.

An accelerometer apparatus-cable connector 54 is mounted on the proximal end of accelerometer apparatus 50 so as to couple accelerometer apparatus 50 to cable 13.

A male threaded projection 68 is formed on the proximal end of accelerometer apparatus housing 62. A corresponding female threaded bore 70 is formed in the distal end of guide sleeve 56. Optional guide sleeve 56 may then be threaded onto projection 68 so as to surround and restrain the lateral movement of connector 54, while allowing cable 13 to pass outwardly from the proximal end of the sensing head 12.

By the above-described preferred construction of the sensing head 12, such sensing head 12 may be utilized to conveniently sense vibrationally energy emanating from the distal end DE of catheter 20 or from the distal end of the ultrasound horn of transducer 24.

c. Preferred Monitor Apparatus

In the preferred embodiment of the present invention, the monitor 14 comprises a vibration meter apparatus such as PCB series 291 available from PCB Electronics, 3425 Walden Avenue, Depew, N.Y. 14043-2495. The monitor 14 may optionally have custom indicia formed thereon to indicate a Fail/Pass condition. Additionally, the range selector switch may optionally comprise indicia indicative of the particular ultrasound therapeutic procedure to be performed. Thus, according to the setting of the range selector switch, the vibration signal received by the meter is attenuated or amplified, as necessary, so as to provide an indication of acceptability thereof according to the particular ultrasound therapeutic procedure to be performed.

d. Preferred Methods of Using the Vibration Measuring Device of the Present Invention The above-described device 10 may be utilized in various clinical applications for testing the operability and efficiency of an ultrasound transmitting member or ultrasound catheter 20.

Figure 5:
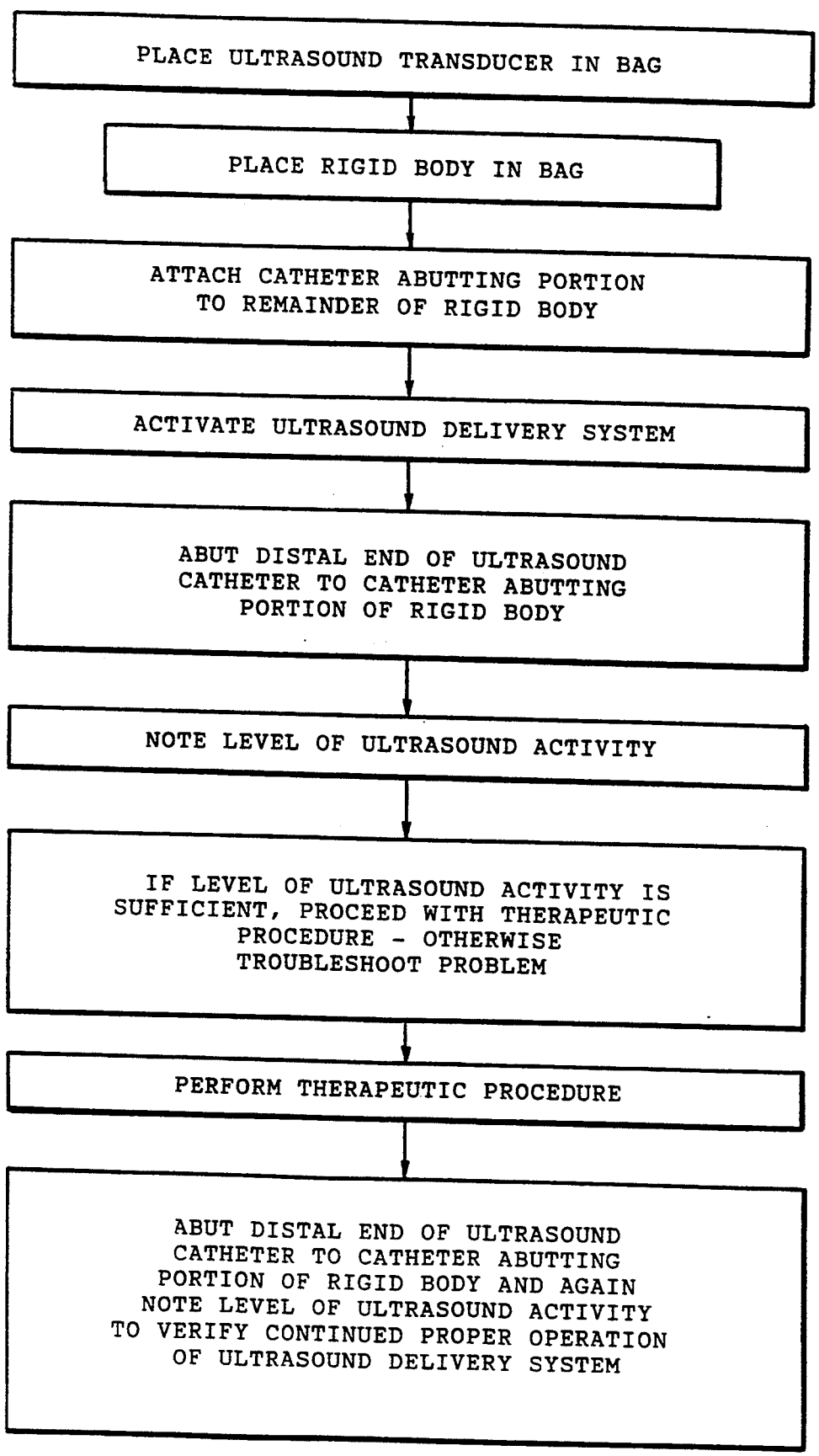
FIG. 5 is a flow chart illustrating the steps for performing a therapeutic procedure utilizing the method for measuring ultrasound activity in an ultrasound delivery system according to the present invention.
Figure 2:
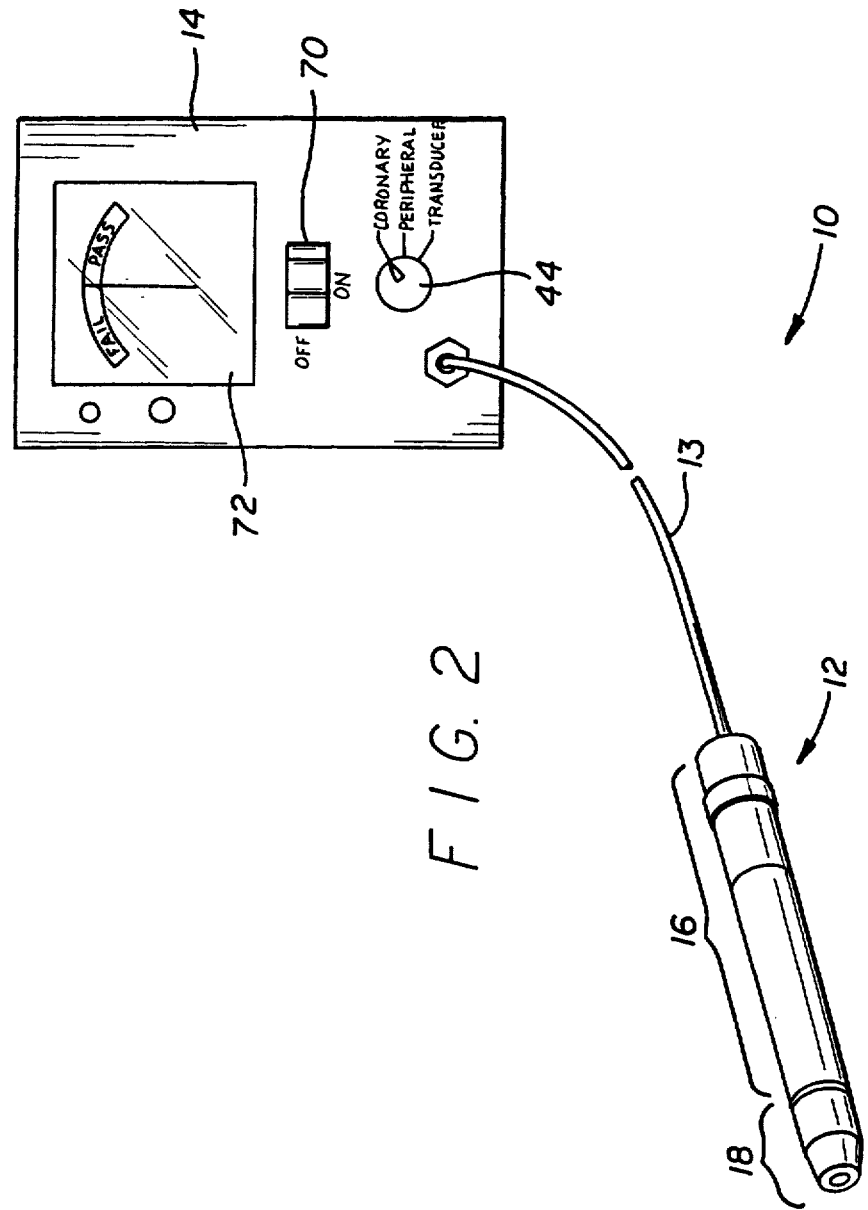
Figure 3:
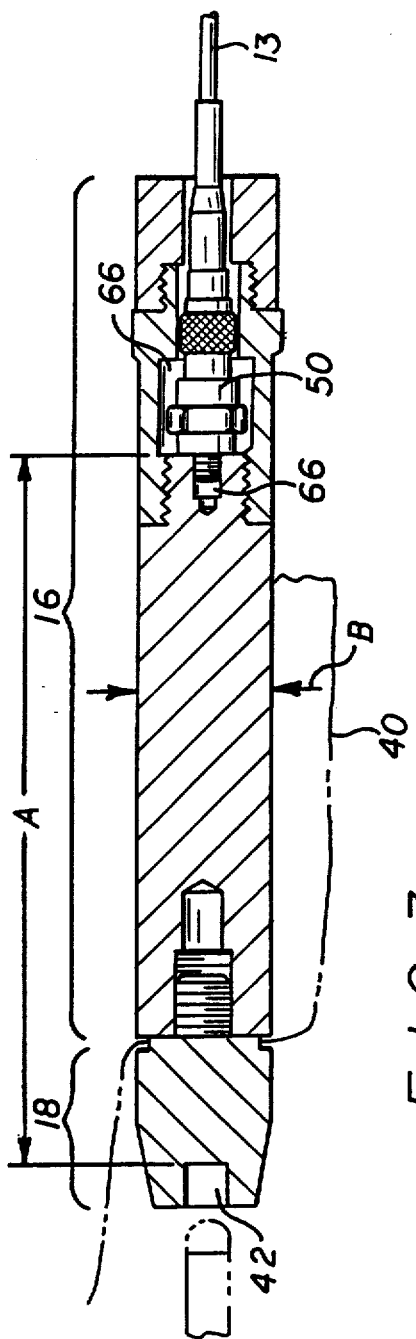
Figure 4:
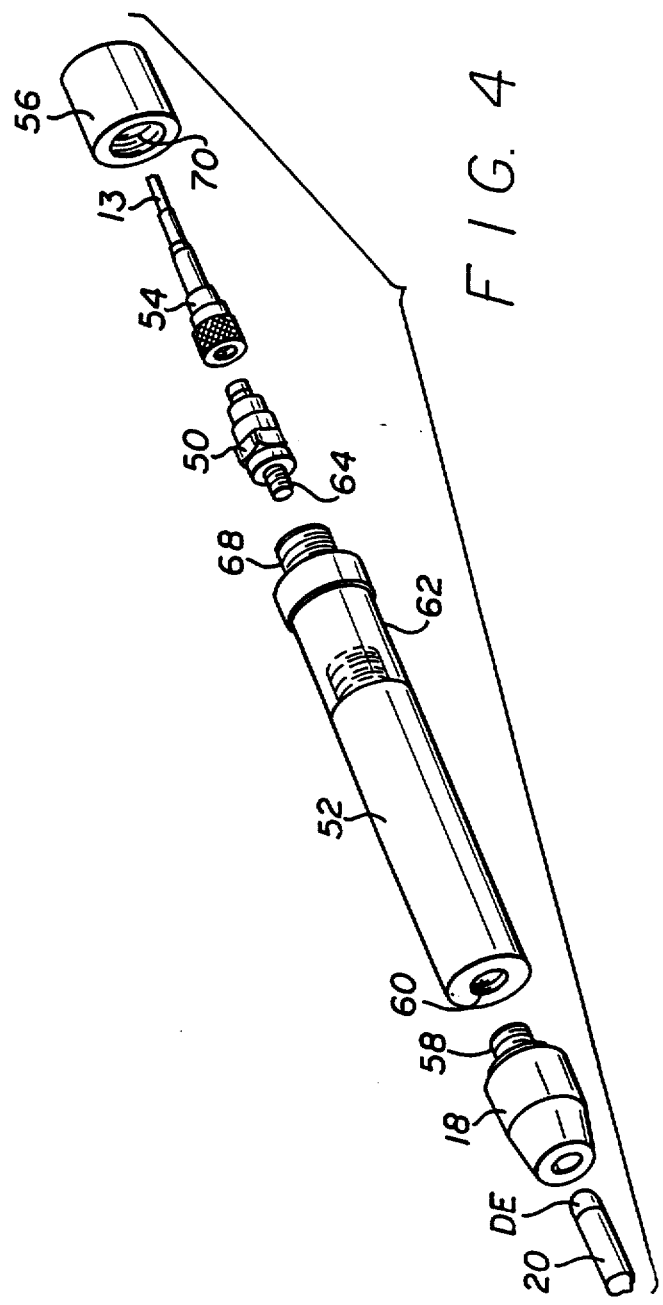

A method for testing an ultrasound catheter prior to (and preferably also after) therapeutic use is shown in the block diagram of FIG. 5.

More specifically, with reference to FIGS. 1 and 2, the ultrasound catheter 20 shown may be tested prior to use in a coronary artery ablation procedure by the following steps:

Step 1. Connect ultrasound transducer 24 to signal generator 28 by cable 26.

Step 2. Set signal generator 28 at desired output level for coronary ablation procedure.

Step 3. Connect accelerometer apparatus housing portion 16 of sensing head 12 to monitor 14 by way of cable 13. Set monitor 14 on "coronary" setting and turn on/off switch 70 to "on" position.

Step 4. Insert accelerometer apparatus housing portion 16 of sensing head 12 into sterile barrier bag 40.

Step 5. Position disposable end member 18 on outside of sterile barrier bag 40 adjacent distal end of accelerometer apparatus housing portion 16 and threadably mount abutment end member 18 onto accelerometer apparatus housing portion 16 thereby pinching the surrounding portion of sterile barrier sack 14 therebetween. The male threads 58 of the abutment end member 18 may penetrate the bag 40 or the bag 40 may alternatively remain intact, captured intermediate the abutment end member 18 and the accelerometer housing portion 16.

Step 6. Operatively connect the proximal connector assembly 22 of catheter 20 to the ultrasound transducer 24.

Step 7. Insert the distal end DE of catheter 20 into the receiving recess 42 of sensing head 12 such that the distal end DE of the catheter 20 is in firm abutment with the floor of the receiving recess 42.

Step 8. Depress foot on/off pedal 30 thereby actuating signal generator 28 so as to cause ultrasound transducer 24 to send ultrasonic vibration through catheter 20.

Step 9. Observe the display 72 of monitor 14 to determine whether the sensing head 12 has sensed ultrasonic vibration at the distal end DE of the catheter 20 which is within the acceptable or "pass" range.

Step 10. If the monitor 14 indicates that the ultrasound vibration at the distal end DE of catheter 20 is within the acceptable or "pass" range, the catheter 20 may then be inserted into the vasculature and advanced to the desired coronary location for purposes of effecting the therapeutic application.

Step 11. If, however, the monitor 14 indicates that the ultrasound vibration sensed at the distal end DE of the catheter 20 is within the unacceptable or "fail" range, appropriate steps may then be taken to troubleshoot the system and/or to change the catheter 20 prior to proceeding with the therapeutic procedure.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

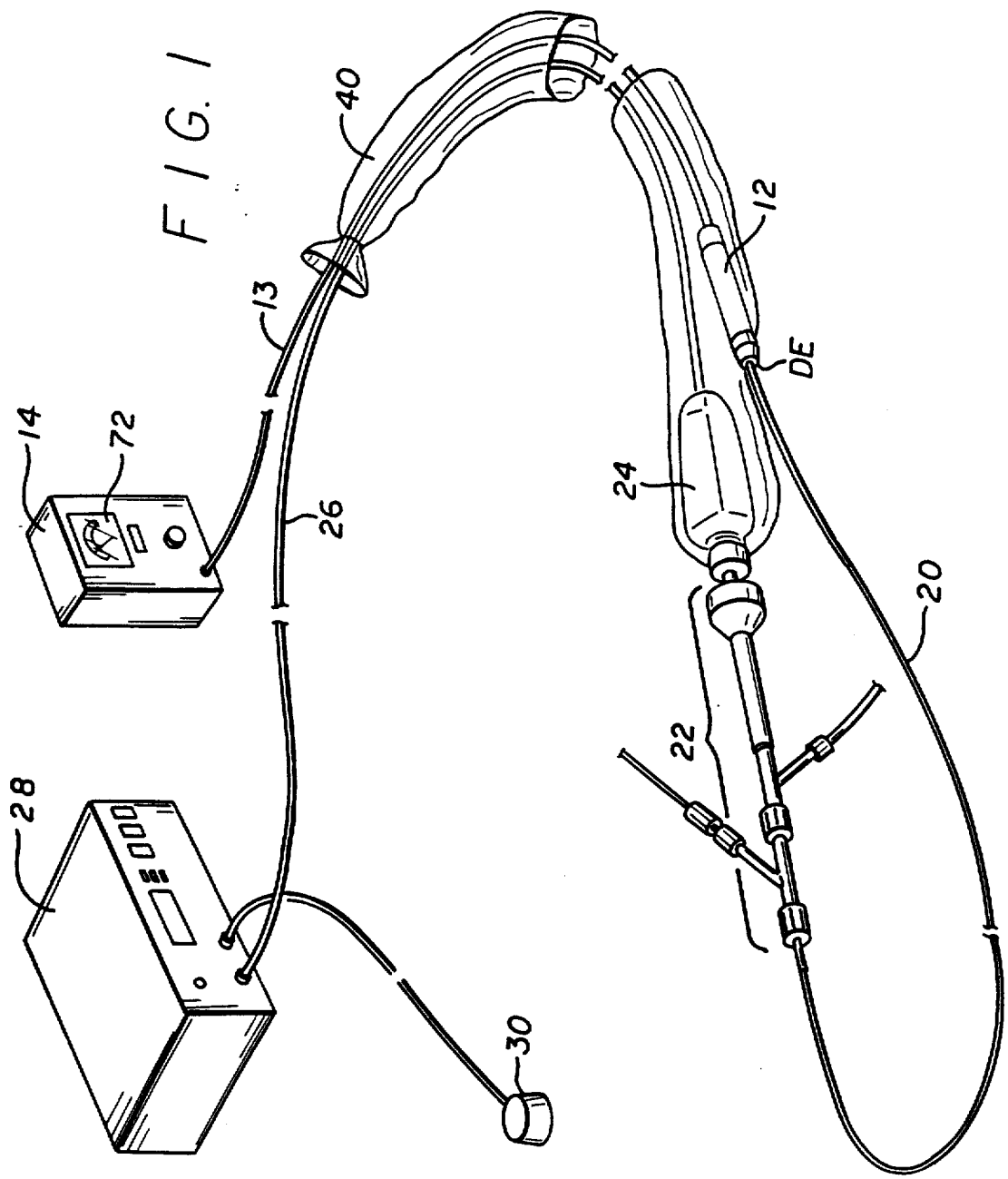

What is claimed is:

1. An improved therapeutic ultrasound delivery system comprising:
   a) an ultrasound signal generator for providing an ultrasound drive signal;
   b) an ultrasound transducer receiving the ultrasound drive signal for converting the ultrasound drive signal into ultrasound vibration;
   c) an ultrasound catheter, having proximal and distal ends, attached at the proximal end to the ultrasound transducer, for transmitting ultrasound vibration from the ultrasound transducer to effect treatment at a desired anatomical site; and
   d) a device for measuring ultrasonic activity at the distal end of the catheter to verify proper operation of the ultrasound generator, the ultrasound transducer, and the catheter.

2. The system of claim 1 wherein the device for measuring ultrasonic activity of the distal end of the catheter comprises:
   a) a sensor for providing an output representative of a sensed ultrasound vibration level;
   b) an indicator receiving the output of the sensor and providing an indication of the vibration level sensed thereby;
   c) a rigid body to which the sensor is attached, the rigid body comprising:
      i) a sensor attaching portion;
      ii) a catheter abutting portion configured to abut the distal end of the catheter; and
   d) wherein ultrasonic activity of the ultrasound delivery system is measured by abutting the distal end of the catheter to the catheter abutting portion of the rigid body and noting the indication provided by the indicator.

3. The system of claim 2 wherein the sensor comprises an accelerometer apparatus.

4. The system of claim 2 wherein the indicator comprises a meter apparatus.

5. The system of claim 2 wherein:
   a) the sensor attaching portion comprises a female threaded coupling;
   b) the sensor comprises a male thread coupling engaging the female threaded coupling; and
   c) the catheter abutting portion comprises a recess configured to receive the distal end of the catheter.

6. The system of claim 2 wherein the catheter abutting portion is removably and rigidly attachable to the sensor attaching portion so as to facilitate placement of the sensor attaching portion upon one side of a sterile barrier and placement of the catheter abutting portion upon the opposite side of the sterile barrier.

7. The system of claim 6 wherein the catheter abutting portion is maintained in a sterile condition by the sterile barrier prior to use.

8. The system of claim 6 wherein the catheter abutting portion is disposable.

9. The system of claim 2 wherein the indicator is configured to provide an indication of the condition of ultrasound delivery system providing various different desired ultrasonic activity levels to accommodate various different therapeutic procedures.

10. The system of claim 9 wherein the indication of the condition of ultrasound delivery systems comprises a fail/pass type of indication.

11. The system as in claim 10 wherein the indicator comprises a selector for selecting the type of procedure that the ultrasound delivery system is to be utilized in, the indication of the condition of the ultrasound delivery system being responsive to the the selector.

12. An improved therapeutic ultrasound delivery system comprising:
   a) an ultrasound signal generator for providing an ultrasound drive signal;
   b) an ultrasound transducer receiving the ultrasound drive signal for converting the ultrasound drive signal into ultrasound vibration;
   c) an ultrasound catheter, having proximal and distal ends, attached at the proximal end to the ultrasound transducer, for transmitting ultrasound vibration from the ultrasound transducer to effect treatment at a desired anatomical site; and
   d) a device for measuring ultrasonic activity of the distal end of the catheter, the device comprising:
      i) an accelerometer apparatus for providing an output representative of a sensed vibration level;
      ii) a meter apparatus receiving the output of the accelerometer apparatus and providing an indication of the sensed vibration level;
      iii) a rigid body comprising an accelerometer apparatus attaching portion to which the accelerometer apparatus is attached and a disposable catheter abutting portion comprising a recess configured to receive the distal end of the catheter, the catheter abutting portion being removably and rigidly attachable to the accelerometer apparatus attaching portion and disposed upon one side of a sterile barrier and the catheter abutting portion disposed upon the opposite side of the sterile barrier;
   e) wherein the device for measuring ultrasonic activity verifies proper operation of the ultrasound generator, the ultrasound transducer, and the catheter by measuring ultrasonic activity at the distal end of the catheter.

13. A method for measuring ultrasonic activity in a therapeutic ultrasound delivery system, the method comprising the steps of:
   a) activating the ultrasound delivery system;
   b) abutting a distal end of an ultrasound catheter of the ultrasound delivery system to a device for measuring ultrasonic activity;
   c) noting the level of ultrasonic activity as indicated by an indicator responsive to the device for measuring ultrasonic activity;
   d) inserting the distal end of the catheter into a patient's vasculature;
   e) advancing the distal end of the catheter to a desired location within the patient's vasculature; and
   f) applying ultrasound energy to effect treatment at the desired location.

14. The method of claim 13 further comprising the step of selecting a desired procedure to be performed, the indicator being responsive to such selection so as to indicate whether the measured level of ultrasonic activity is sufficient for performance of the selected procedure or is insufficient for the performance of the selected procedure.

15. The method of claim 13 wherein the step of noting the level of ultrasonic activity comprises noting a fail/pass indication provided by the indicator.

16. The method as recited in claim 13 wherein the step of abutting a distal end of an ultrasound catheter to a device for measuring ultrasonic activity comprises abutting the distal end of the catheter to a catheter abutting portion formed from a rigid body, the rigid body having a sensor attached thereto for providing an output to the indicator representative of the level of ultrasound vibration sensed thereby.

17. The method as recited in claim 16 further comprising the step of attaching the catheter abutting portion to the rigid body so as to capture a sterile barrier therebetween.

18. The method as recited in claim 17 wherein the sterile barrier comprises a bag.

19. The method as recited in claim 17 further comprising the step of maintaining the catheter abutting portion sterile to use.

20. A method for performing a therapeutic ultrasound procedure, said method comprising the steps of:
   a) disposing an ultrasound transducer within a sterile bag such that a sterile ultrasound catheter extends from the bag;
   b) disposing a rigid body having an ultrasound vibration sensor attached thereto within the bag;
   c) attaching a catheter abutting portion of the rigid body thereto such that the catheter abutting portion is disposed outside of the bag;
   d) activating the ultrasound delivery system;
   e) abutting a distal end of an ultrasound catheter of the ultrasound delivery system to a device for measuring ultrasonic activity;
   f) noting the level of ultrasonic activity as indicated by an indicator responsive to the device for measuring ultrasonic activity; and
   g) applying ultrasound energy to effect treatment at an anatomical site.

21. The method of claim 20 further comprising the step of selecting a desired procedure to be performed, the indicator being responsive to such selection so as to indicate whether the measured level of ultrasonic activity is sufficient for performance of the selected procedure or is insufficient for the performance of the selected procedure.

22. The method of claim 20 wherein the step of noting the level of ultrasonic activity comprises noting a fail/pass indication provided by the indicator.

23. The method of claim 20 further comprising the step of again abutting the distal end of the ultrasound catheter to the catheter abutting portion of the rigid body and again noting the level of ultrasonic activity after the step of applying ultrasound energy to an anatomical site.

* * * * *

UNITED STATES PATENT AND TRADEMARK OFFICE
CERTIFICATE OF CORRECTION

PATENT NO. : 5,390,678
DATED : Feb. 21, 1995
INVENTOR(S) : Douglas H. Gesswein, Timothy C. Mills, Pete B. Klumb It is certified that error appears in the above-identified patent and that said Letters Patent is hereby corrected as shown below:

In the drawings, replace "Sheet 1 of 4, Sheet 2 of 4, Sheet 3 of 4", depicting "Fig. 1, Fig. 2, Fig. 3 & Fig. 4", with attached "Sheet 1 of 4, Sheet 2 of 4, Sheet 3 of 4" depicting corrected "Fig.1, Fig. 2, Fig. 3, & Fig. 4".

Column 6, Line 56, Change "20", To read --28--.

Column 9, Line 58, Change "14", To read --40--.

Column 11, Claim 11, Line 35, delete "the", second occurence.

Signed and Sealed this

Fourteenth Day of April, 1998

BRUCE LEHMAN

*Attest:*

*Attesting Officer*     *Commissioner of Patents and Trademarks*